(12) United States Patent
Miller

(10) Patent No.: US 6,503,191 B1
(45) Date of Patent: Jan. 7, 2003

(54) MOLECULAR ABSORPTION RESONANCE SYSTEM

(76) Inventor: Carl W. Miller, 17721 Gulf Blvd., Redington Shores, FL (US) 33708

( * ) Notice: Subject to any disclaimer, the term of this patent is extended or adjusted under 35 U.S.C. 154(b) by 0 days.

(21) Appl. No.: 10/037,328

(22) Filed: Nov. 9, 2001

(51) Int. Cl.[7] .................................................. A61F 2/00
(52) U.S. Cl. .......................................... 600/30; 606/33
(58) Field of Search ..................... 606/33, 34; 607/156; 600/907, 411

Primary Examiner—Michael Peffley
Assistant Examiner—Peter J Vrettakos

(57) ABSTRACT

A molecular absorption resonance system determines the molecular resonant frequency of a subject and destroys the subject. First provided is a first antenna with an associated microwave generator for generating waves and directing such waves to the subject. A second antenna with an associated receiver is next provided for receiving waves from the input antenna and subject for determining the resonant frequency of the subject. Lastly, an output device is provided for transmitting waves at a frequency determined by the receiver and for directing such waves to the subject for destroying the subject.

1 Claim, 5 Drawing Sheets

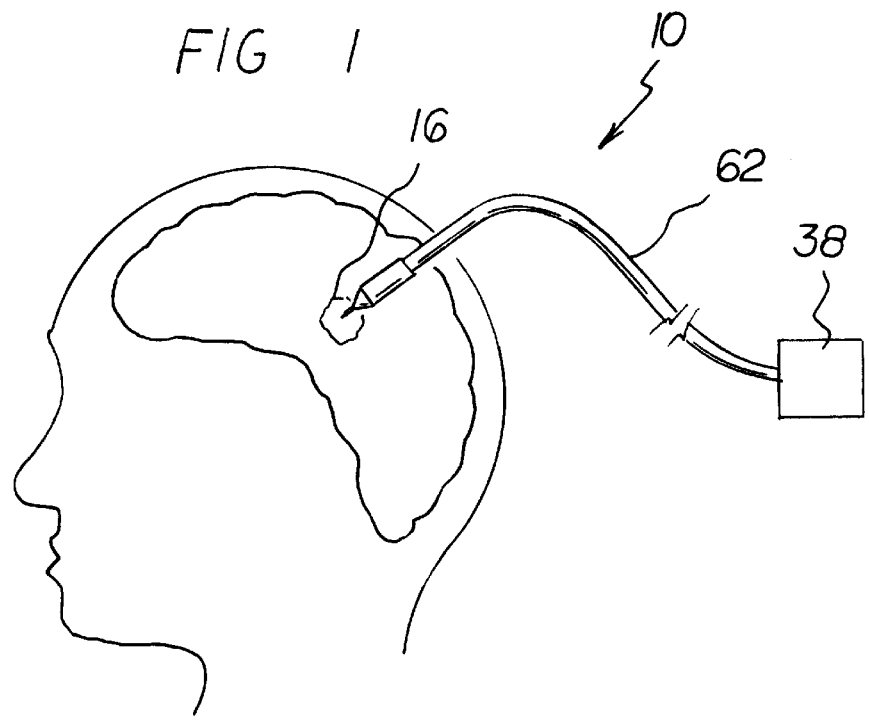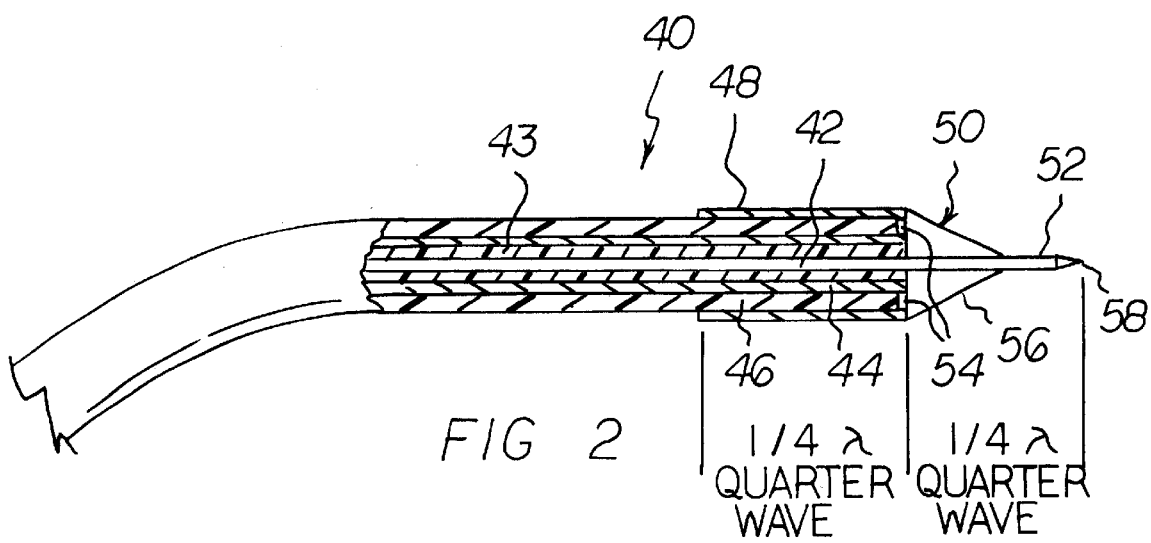

MOLECULAR ABSORPTION RESONANCE SYSTEM

BACKGROUND OF THE INVENTION

1. Field of the Invention

The present invention relates to a molecular absorption resonance system and more particularly pertains to identifying and destroying adverse molecules, cells, and the like, such as cancer, aids and anthrax.

2. Description of the Prior Art

The use of resonance systems of known designs and configurations is known in the prior art. More specifically, resonance systems of known designs and configurations previously devised and utilized for the purpose of identifying or destroying adverse matter through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,307,812 to Hardy discloses a heat surgery system monitored by real-time magnetic resonance profiling. U.S. Pat. No. 5,658,234 to Dunlavy discloses a method for treating tumors. Lastly, U.S. Pat. No. 5,997,477 to Sehgal discloses an apparatus for imaging an element within a tissue and method therefor.

While these devices fulfill their respective, particular objectives and requirements, the aforementioned patents do not describe a molecular absorption resonance system that allows identifying and destroying adverse molecules, cells, and the like.

In this respect, the molecular absorption resonance system according to the present invention substantially departs from the conventional concepts and designs of the prior art, and in doing so provides an apparatus primarily developed for the purpose of identifying and destroying adverse molecules, cells, and the like.

Therefore, it can be appreciated that there exists a continuing need for a new and improved molecular absorption resonance system which can be used for identifying and destroying adverse molecules, cells, and the like. In this regard, the present invention substantially fulfills this need.

SUMMARY OF THE INVENTION

In view of the foregoing disadvantages inherent in the known types of resonance systems of known designs and configurations now present in the prior art, the present invention provides an improved molecular absorption resonance system. As such, the general purpose of the present invention, which will be described subsequently in greater detail, is to provide a new and improved molecular absorption resonance system and method which has all the advantages of the prior art and none of the disadvantages.

To attain this, the present invention essentially comprises a molecular absorption resonance system 10 comprised of a plurality of components. Such components in their broadest context include a first antenna with an associated microwave generator, a second antenna with an associated receiver, and an output device. Such components are individually configured and correlated with respect to each other so as to attain the desired objective.

The molecular absorption resonance system is for the detection and selective destruction of unwanted molecules and cells. First provided is a frequency determining apparatus. The frequency determining apparatus is adapted to determine the resonant frequency associated with a desired specimen from the unwanted molecules and cells. The frequency determining apparatus includes a specimen holder covered by a pair of low loss dielectric sheets. The sheets include an upper sheet in a plane above the specimen and a lower sheet in a plane below the specimen. The frequency determining apparatus also includes a focused beam illumination antenna positioned above the specimen and the upper dielectric sheet. The focused beam illumination antenna has an automatic frequency tuning microwave generator. The frequency tuning microwave generator is adapted to produce a range of waves to radiate the sample. A first display mechanism is coupled to the generator to show the frequencies being transmitted. The frequency determining apparatus also includes a receiving antenna positioned below the specimen and lower dielectric sheet. The receiving antenna is adapted to capture the transmitted signal after passing through the specimen. A receiver is coupled to the receiving antenna. A second display mechanism is coupled to the receiver and also coupled to the first display mechanism and microwave generator to show the frequencies of the specimens being absorbed. The frequency determining apparatus also includes a temperature sensor in proximity to the specimen and coupled to the first display mechanism for determination of the resonant frequency of the subject molecules. Next provided is a tunable frequency generating source. The tunable frequency generating source has a control mechanism from the field of frequency controllers including but not limited to frequency meters and phase-locking crystal controlled references. The tunable frequency generator is adapted to create a suitable signal with an appropriate frequency to destroy unwanted molecules and cells corresponding to the specimen. The appropriate frequency is determined by the detected and determined resonant frequency found by the frequency determining apparatus. Lastly, an output device is provided. The output device includes a metal central conductor. A plurality of sheaths surround the conductor. The sheaths include an added conventional smooth sleeve welded to the outer conductor braid. The output device further includes an applicator. The applicator has a penetrating tip welded to the center conductor. The exposure of the smooth sleeve conductor and center conductor tip is correlated with the quarter wave length. A tapered dielectric partially conceals the exposed conductor for facilitating the immersion of the conductor in situ. The exposed conductor is shaped with a surgically sharpened point to facilitate the process. The output further includes a treatment applicator formed from a specialized dielectric. An electrical line couples the output device and the tunable frequency generating source.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved molecular absorption resonance system which has all of the advantages of the prior art resonance systems of known designs and configurations and none of the disadvantages.

It is another object of the present invention to provide a new and improved molecular absorption resonance system which may be easily and efficiently manufactured and marketed.

It is further object of the present invention to provide a new and improved molecular absorption resonance system which is of durable and reliable constructions.

An even further object of the present invention is to provide a new and improved molecular absorption resonance system which is susceptible of a low cost of manufacture with regard to both materials and labor, and which accordingly is then susceptible of low prices of sale to the medical and scientific community, thereby making such molecular absorption resonance system economically available to the buying public.

Even still another object of the present invention is to provide a molecular absorption resonance system for identifying and destroying adverse molecules, cells, and the like.

Lastly, it is an object of the present invention to provide a new and improved system for determining the molecular resonant frequency of a subject and for destroying the subject. First provided is a first antenna with an associated microwave generator for generating waves and directing such waves to the subject. A second antenna with an associated receiver is next provided for receiving waves from the input antenna and subject for determining the resonant frequency of the subject. Lastly, an output device is provided for transmitting waves at a frequency determined by the receiver and for directing such waves to the subject for destroying the subject.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a side elevational view of a molecular absorption resonance system output device constructed in accordance with the principles of the present invention.

FIG. 2 is a cross sectional view of the output device shown in FIG. 1.

The same reference numerals refer to the same parts throughout the various Figures.

DESCRIPTION OF THE PREFERRED EMBODIMENT

Figure 3:
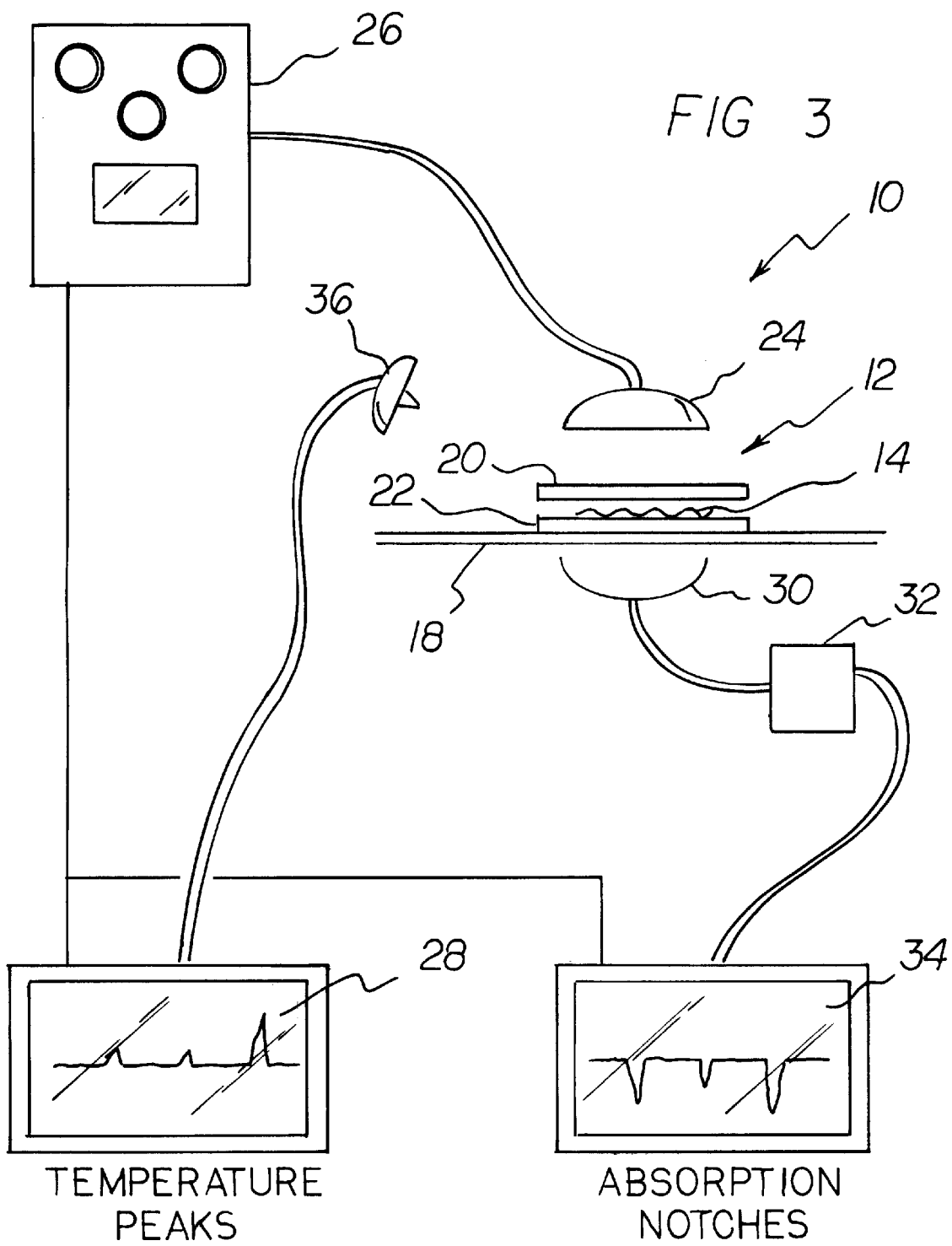
FIG. 3 is a side elevational view of the frequency determining apparatus for the system of the prior Figures.

With reference now to the drawings, and in particular to FIG. 1 thereof, the preferred embodiment of the new and improved molecular absorption resonance system embodying the principles and concepts of the present invention and generally designated by the reference numeral 10 will be described.

The present invention, the molecular absorption resonance system 10 is comprised of a plurality of components. Such components in their broadest context include a first antenna with an associated microwave generator, a second antenna with an associated receiver, and an output device. Such components are individually configured and correlated with respect to each other so as to attain the desired objective.

The primary embodiment of the present invention is shown in FIGS. 1, 2 and 3. From an overview standpoint, FIG. 1 is a side elevational view of a output device being applied to an affected region of molecules and cells. The output device is designed to transmit a resonant frequency signal produced by a tunable frequency generating source. This resonant frequency signal, being identical to the resonant frequency associated with the affected cells, enables the output device to destroy the affected cells. FIG. 2 is a cross sectional view of the output device showing the various sheaths around the metal central conductor. This metal central conductor transmits the resonant frequency signal to the affected area. This cross sectional view also shows the tapered end which facilitates the invasion into a patient. FIG. 3 shows a side elevational view of the frequency determining apparatus. An affected sample is placed in a specimen holder and bombarded with a spectrum of frequencies. A receiver is adapted to collect the transmitted frequencies which will reflect the frequencies absorbed by the specimen.

More specifically, the molecular absorption resonance system 10 is for the detection and selective destruction of unwanted molecules and cells 16. First provided is a frequency determining apparatus 12. The frequency determining apparatus is adapted to determine the resonant frequency associated with a desired specimen 14 from the unwanted molecules and cells. The frequency determining apparatus includes a specimen holder 18 covered by a pair of low loss dielectric sheets. The sheets include an upper sheet 20 in a plane above the specimen and a lower sheet 22 in a plane below the specimen. The frequency determining apparatus also includes a focused beam illumination antenna 24 positioned above the specimen and the upper dielectric sheet. The focused beam illumination antenna has an automatic frequency tuning microwave generator 26. The frequency tuning microwave generator is adapted to produce a range of waves to radiate the sample. A first display mechanism 28 is coupled to the generator to show the frequencies being transmitted. The frequency determining apparatus also includes a receiving antenna 30 positioned below the specimen and lower dielectric sheet. The receiving antenna is adapted to capture the transmitted signal after passing through the specimen. A receiver 32 is coupled to the receiving antenna. A second display mechanism 34 is coupled to the receiver and also coupled to the first display mechanism and microwave generator to show the frequencies of the specimens being absorbed. Resonance absorption frequency will be shown by a decrease in microwave energy transmitted through the specimen. Also, by increase in temperature measured by the heat sensor. The frequency determining apparatus also includes a temperature sensor 36 in proximity to the specimen and coupled to the first display mechanism for additional measurement of resonance absorption frequencies.

Next provided is a tunable frequency generating source 38. The tunable frequency generating source has a control mechanism from the field of frequency controllers including but not limited to frequency meters and phase-locking crystal controlled references. The tunable frequency generator is adapted to create a suitable signal with an appropriate frequency to destroy unwanted molecules and cells corresponding to the specimen. The appropriate frequency is determined by the detected and determined resonant frequency found by the frequency determining apparatus.

Lastly, an output device 40 is provided. The output device includes a metal central conductor 42. A plurality of sheaths surround the conductor. The sheaths include an added conventional smooth metal sleeve 48 welded at 54 to an outer conductor braid 44. A dielectric insulating inner sheath 43 is interior of the braid and a coaxial dielectric 46 exterior of the braid. The output device further includes an applicator 50. The applicator has a penetrating tip 52 welded to the center conductor with a tapered dielectric 56 adjacent to the tip. Exposure of the smooth sleeve conductor and center conductor tip are correlated with a quarter wave length. A tapered dielectric 56 partially conceals the exposed conductor for facilitating the immersion of the conductor in situ. The exposed conductor is shaped with a sharpened point 58 to facilitate the process. The output further includes a treatment applicator formed from a specialized dielectric. An electrical line 62 couples the output device and the tunable frequency generating source.

Figure 4:
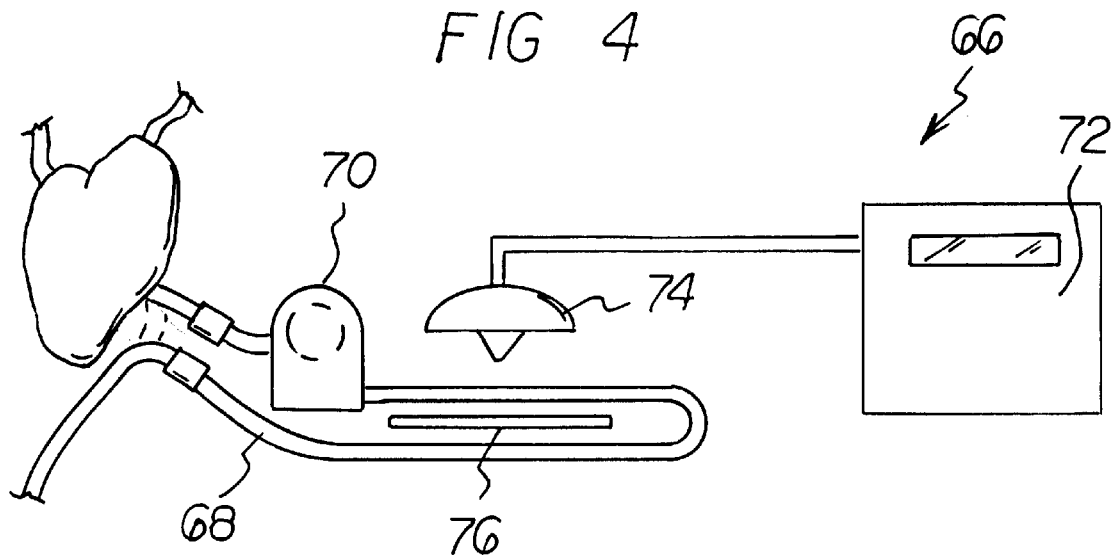
FIG. 4 is an alternative embodiment of the present invention wherein the affected specimen is found within the blood stream.

FIG. 4 illustrates an alternate embodiment of the invention wherein the affected specimen is found within the blood stream. To selectively destroy these specimens their resonant frequency would be found using a similar method as disclosed above. Then a modified output device would utilized to destroy the adverse molecules, cells and the like.

More specifically, this alternate embodiment is an output device 66 for eradicating affected unwanted molecules and cells with an associated resonant frequency within circulating blood. First provided in this embodiment is a shunt tubing 68. The tubing is fabricated of low dielectric loss surgical bypass tubing. An associated pump 70 is adapted to remove blood from its native vessel, such as the aorta, and transmit the blood out of the body and then return the blood back to its native vessel.

In this alternate embodiment, a microwave generator 72 is next provided. The microwave generator is adapted to produce a resonant frequency signal, preferably determined as in the primary embodiment described above, associated with a specimen from the affected unwanted molecules and cells and designed to destroy the affected unwanted molecules and cells.

Next, in this embodiment, a modified focused array antenna 74 is positioned adjacent to the tubing and is coupled to the microwave generator. The antenna is adapted to transmit the resonant frequency signal.

Finally, in this embodiment, an absorbent material surface 76 is positioned adjacent to the tubing opposite the antenna. The absorbent material surface is adapted to collect unabsorbed and stray signals from the antenna.

Figure 5:
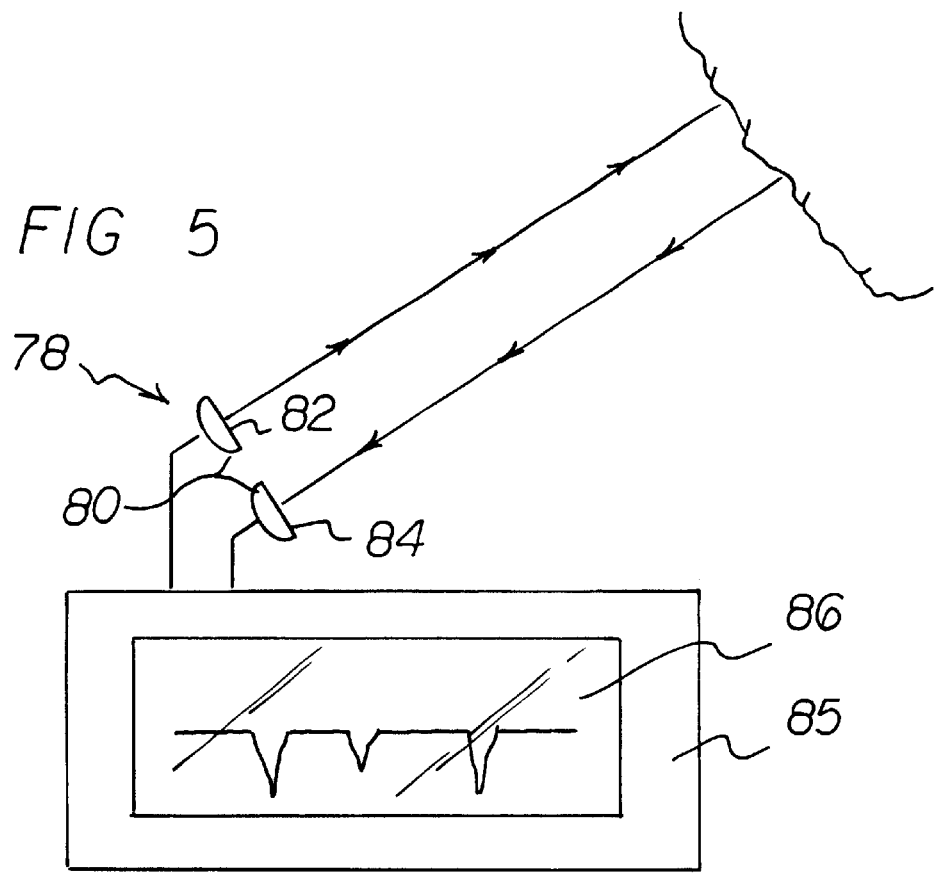
FIG. 5 is another alternate embodiment of the present invention wherein chemical and biological contaminations in the atmosphere can be detected.

FIG. 5 shows another alternate embodiment of the present invention wherein chemical and biological contaminations in the atmosphere can be detected at great distances from the probe site. In such embodiment, a molecular absorption resonance system 78 for the detection and decontamination of chemical and/or biological warfare material, a rotatable radar housing 80 is first provided. The housing has a focused beam illumination antenna portion 82 and a receiving antenna portion 84. The focused beam illumination antenna portion 82 is adapted to transmit a signal.

Next provided in this embodiment is an automatic frequency tuning microwave generator/receiver 84. The microwave generator is coupled to the focused beam illumination antenna portion and is adapted to produce a range of waves to radiate the sample. The receiving antenna portion 82 is adapted to capture any reflected transmitted signal being bounced off of samples of any chemical and/or biological warfare material in the air. The generator/receiver is coupled to the receiving antenna portion to process the signal.

Lastly, in this embodiment, a display mechanism 86 is provided. The display mechanism provides a visual display of the frequency versus amplitude to show what frequencies were absorbed. Such absorbed frequencies are unique to various samples.

Figure 6:
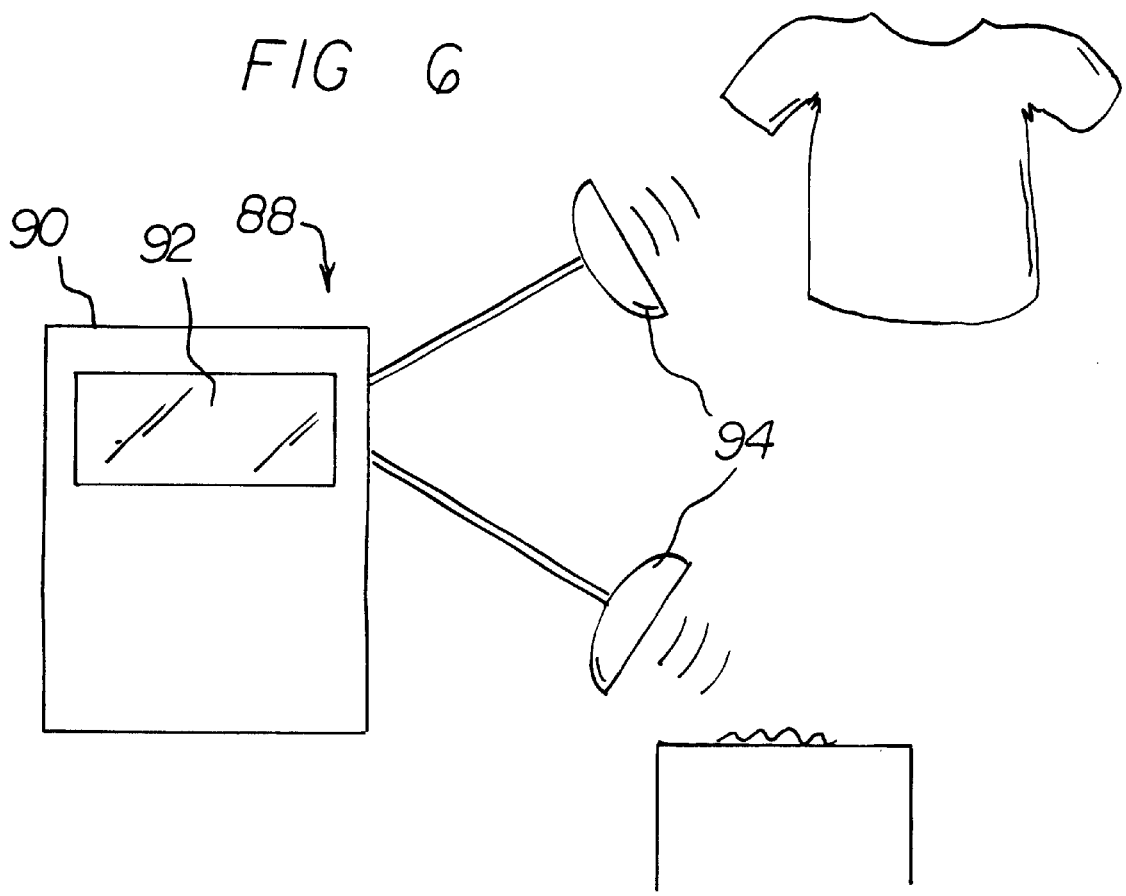
FIG. 6 is yet another alternate embodiment of the present invention adapted to decontaminate various objects.

An additional alternate embodiment is illustrated in FIG. 6 which shows an embodiment adapted to decontaminate various objects such as clothing on a person. The resonant frequency of affected molecule and cells, having been first determined, objects can be rendered free of these known contaminates without destroying the objects themselves. At molecular resonance frequencies, the contaminant molecules will absorb the microwave energy at a 10 to 100 times greater rate than the non-resonant substrates such as clothing. Thus, thermal dissociation may occur without unduly heating of the host material. With greater specificity, a decontamination system 88 is for various objects given the knowledge of the contaminates resonant frequency.

Next provided, in this additional embodiment, is a tunable frequency generating source 90. The frequency generating source has a control mechanism adapted to create a suitable signal with an appropriate frequency to destroy the contaminate. Such appropriate frequency is determined by the detected/determined resonant frequency, preferably detected/determined as in the primary embodiment. The source includes a display panel 92.

Lastly, in this additional embodiment, an output device 94 is provided. The output device is comprised of at least one concaved disk or phased array antenna. The antenna is adapted to transmit the appropriate frequency signal to contaminated objects with antenna having a variable illumination pattern correlated to its output signal.

Figure 7:
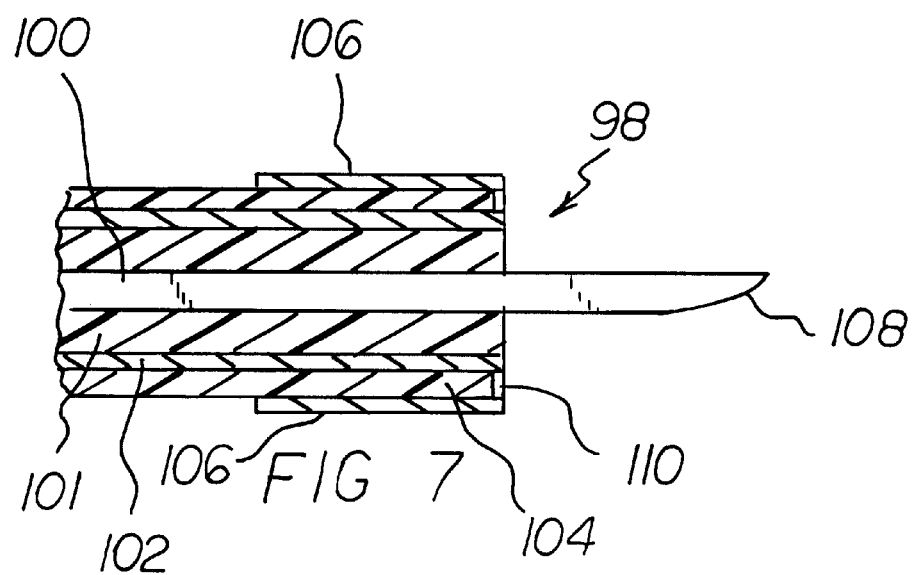
FIG. 7 is one many variations of output or antenna types that may be associated with the present invention.

FIG. 7 illustrates one of many variations of output or antenna types that may be associated with this invention. This antenna and other medical applicators are designed for hyperthermia treatment and taking into consideration or utilizing malignant molecular resonance absorption frequencies. This basic example shows a folded back coaxial quarter wave dipole. More specifically, a medical output device 98 is for transmitting signals to malignant molecules and cells. A cylindrical metal central conductor 100 is provided to radiate a signal. A quarter wave metal sleeve 106 is welded to the outer conductor braid 102 and folded back over the outer insulating coaxial sheath 104 over the braid and an inner insulating sheath 101 beneath the braid. The metal sleeve and metal sleeve are welded at 110. An applicator has a pointed tip 108 welded to an end of the center conductor and is of quarter wavelength.

Figure 8:
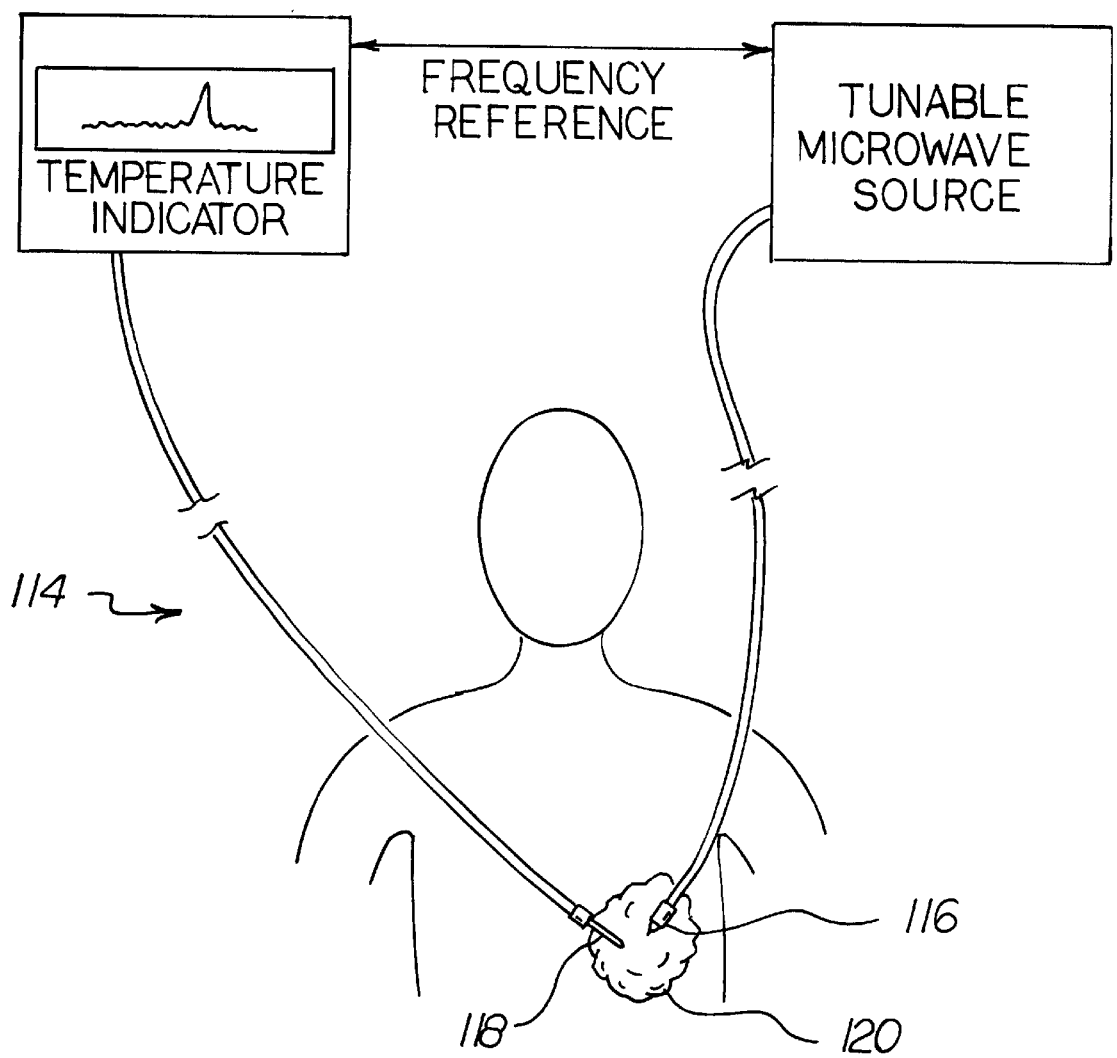
FIG. 8 is a schematic illustration of the final embodiment of the invention.

An alternative approach to removal of samples of malignant tissue material, then measurement of molecular resonance absorption by manual or automatic tuning, then irradiating the tissue mass at these resonant frequencies is shown in FIG. 8. This embodiment of FIG. 8 involves a system 114. Simultaneously inserting the penetrating microwave radiating antenna 116 and a penetrating temperature sensor probe 118 into primary malignant mass 120. The same approach can, of course, be used for surface irradiation and surface temperature observation when such surfaces are exposable.

There have been, and there continue to be, successful treatments of cancer by hyperthermia, that is heating to elevated temperatures. Of these successes, some have been by simple hot water bath immersion, but most, in fact have been by heating with electromagnetic wave (commonly called radio waves or microwaves) induced heating, exactly the same as in a microwave oven.

This has been in these limited cases successfully accomplished without undue destruction of adjacent healthy molecules/cells because malignant cells are destroyed at temperatures a few degrees below that for healthy cells, some reports estimate, 5 degrees to 6 degrees Fahrenheit lower. Destruction of the malignant cells is indicated in the vicinity of 109 degrees to 110 degrees Fahrenheit.

A margin of only 5 degrees to 6 degrees Fahrenheit is obviously small and dangerous, and a larger amount is extremely desirable. The present invention contains the description of equipment needed and the methodology of it is employed to achieve exactly this condition, that is: to irradiate adjacent and even co-mingled malignant and healthy molecules/cells with the malignant cells absorbing 10 to 100 times as much microwave energy as adjacent healthy cells and transforming it to 10 to 100 times greater absorbed heat.

The basic physical reason for achieving this condition is as follows: all molecules thus far measured, organic and inorganic have a unique family of spin and vibration resonance frequencies. When irradiated at exactly, or very nearly, one or any number of these frequencies, by electromagnetic (EM) waves, resonance absorption occurs transforming the EM energy into heat energy.

There is scientific theory to essentially assure that all molecules must have unique resonance frequencies. There is scientific reason to expect that no differing molecules will have the same resonance frequencies. Therefore, when we measure as herein described, the family of resonance frequencies, such as carcinoma, melanoma, etc. and irradiate these growths at one or more of these resonant frequencies and irradiate these growths at one or more of these resonant frequencies, they will absorb EM energy and transform it to heat energy at 110 to 100 (based on measured data of known molecules) times greater rate than "OFF" (randomly selected) frequencies that have been heretofore used and 10 to 100 times greater than adjacent healthy cells.

Various embodiments are disclosed herein for detecting material of a particular resonant frequency and/or determining the resonant frequency of a particular material and/or destroying a particular material of a particular resonant frequency. It should be understood that any of the destroying techniques could be utilized after any of the detecting or determining techniques. Similarly, any of the detecting or determining or destroying techniques could be used independently of the other techniques.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A molecular absorption resonance system for the detection and selective destruction of unwanted molecules and cells comprising, in combination;

a frequency determining apparatus adapted to determine the resonant frequency associated with a desired specimen from the unwanted molecules and cells, such frequency determining apparatus including a specimen holder covered by a pair of low loss dielectric sheets including an upper sheet in a plane above the specimen and a lower sheet in a plane below the specimen, such frequency determining apparatus also including a focused beam illumination antenna positioned above the specimen and the upper dielectric sheet, the focused beam illumination antenna having an automatic frequency tuning microwave generator adapted to produce a range of waves to radiate the sample and with a first display mechanism coupled to the generator to show the frequencies being transmitted, the frequency determining apparatus also including a receiving antenna positioned below the specimen and lower dielectric sheet adapted to capture the transmitted signal after passing through the specimen with a receiver coupled to the receiving antenna and with a second display mechanism coupled to the receiver and also coupled to the first display mechanism and microwave generator to show the frequencies of the specimens being absorbed, the frequency determining apparatus also including a temperature sensor in proximity to the specimen and coupled to the first display mechanism for additional measurement of resonance absorption frequencies;

a tunable frequency generating source having a control mechanism from the field of frequency controllers including but not limited to frequency meters and phase locking crystal controlled references, the tunable frequency generator adapted to create a suitable signal with an appropriate frequency to destroy unwanted molecules and cells corresponding to the specimen, such appropriate frequency being determined by the detected and determined resonant frequency found by the frequency determining apparatus; and an output device including a metal central conductor with a plurality of sheaths surrounding the conductor, including an added conventional smooth sleeve welded to the outer conductor braid with the output device further including an applicator having a penetrating tip welded to the center conductor, exposure of the smooth sleeve conductor and center conductor tip being correlated with a quarter wave length, with a tapered dielectric partially concealing the exposed conductor for facilitating the immersion of the conductor in situ, the exposed conductor being shaped with a point to facilitate the process, the output further including a treatment applicator being formed from a specialized dielectric, and an electrical line coupling the output device and the tunable frequency generating source.

* * * * *